Figure 1:
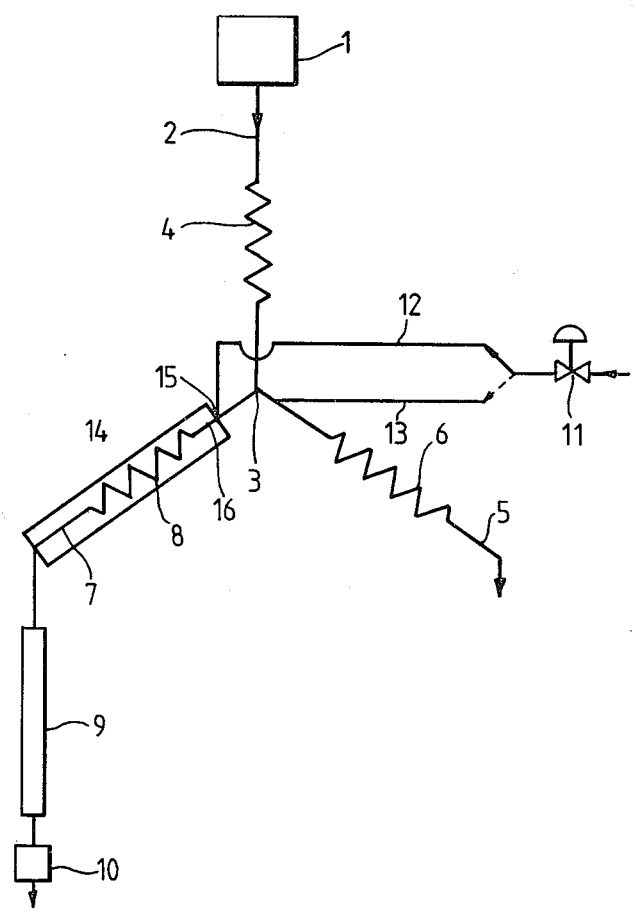

United States Patent [19]

Deans

[11] 4,442,217
[45] Apr. 10, 1984

[54] SAMPLE INJECTION
[75] Inventor: David R. Deans, Nunthorpe, England
[73] Assignee: Imperial Chemical Industries PLC, London, England
[21] Appl. No.: 339,981
[22] Filed: Jan. 18, 1982

Related U.S. Application Data

[63] Continuation of Ser. No. 172,975, Jul. 28, 1980, abandoned.

[30] Foreign Application Priority Data

Aug. 6, 1979 [GB] United Kingdom ............... 7927347

[51] Int. Cl.³ ........................................... G01N 31/08
[52] U.S. Cl. ..................................... 436/161; 55/197; 55/386; 137/561 A; 73/23.1; 436/174; 422/89
[58] Field of Search .............. 436/161, 174, 179, 180, 436/181; 422/88, 89; 73/23, 23.1, 422 GC; 137/561 A; 55/197, 386

[56] References Cited

U.S. PATENT DOCUMENTS

| 3,357,233 | 12/1967 | Roof | 137/819 |
| 3,374,799 | 3/1968 | Lyman | 137/842 |
| 3,426,600 | 2/1969 | Bochinski | 73/422 GC |
| 3,668,834 | 6/1972 | Deans | 73/422 GC |
| 3,712,028 | 1/1973 | Deans | 55/197 |
| 3,753,653 | 8/1973 | Brieva et al. | 422/89 |

FOREIGN PATENT DOCUMENTS 1460390  1/1977  United Kingdom .
1236937  6/1983  United Kingdom .

Primary Examiner—Michael S. Marcus
Attorney, Agent, or Firm—Cushman, Darby & Cushman

[57] ABSTRACT

Samples of substances from sources of variable temperature and pressure are injected into a stream of fluid carrier, for example in chromatographic analysis, without bringing them into contact with moving parts. A stream of the substance is passed through a restriction to the junction of a vent and an injection limb each containing flow restrictions, and carrier fluid is fed alternatively upstream of those restrictions. By thermostatting the injection limb and appropriately selecting the various flow rates constant sized samples may be secured by switching the carrier fluid from the injection limb to the vent for constant times.

6 Claims, 2 Drawing Figures

SAMPLE INJECTION

This is a continuation, of application Ser. No. 172,975 filed July 28, 1980, now abandoned.

This invention relates to sample injection.

In the analysis of materials by chromatography samples are introduced into streams of carrier fluid for analysis. The most common type of chromatographic analysis (gas chromatography) involves the injection of gaseous materials or volatile materials under conditions such that they volatilise into a stream of carrier gas.

The introduction of samples into a stream of carrier fluid may be carried out in a variety of ways; for example when a liquid volatile sample is to be analysed by gas chromatography it may be injected by means of a hypodermic syringe through a septum into a pre-heater in which it volatilises in the presence of a stream of carrier gas. If gaseous samples are to be introduced into a stream of carrier gas or liquid samples are to be introduced into a stream of carrier liquid this may be achieved by a mechanical switching arrangement in which the sample is introduced to the carrier stream by the movement of mechanical components which come into contact with the sample. The latter procedure is subject to a number of disadvantages however. If the sample is corrosive it may affect the mechanism and if the source of the sample is of variable pressure and/or temperature the amount of a gaseous sample injected will be irreproducable.

It is an object of this invention to inject a sample of controlled size from a source which may be a source of gas of variable pressure and/or temperature without bringing it into contact with mechanical moving parts. The invention is particularly applicable to the injection of gas samples into carrier gas streams though it is also applicable to the injection of liquid samples into liquid carrier streams. It may also be used to supply samples for storage or for other forms of analysis.

The invention comprises a method of introducing a sample of controlled quantity into a stream of carrier fluid which comprises passing a stream of a fluid material to be sampled through a restriction to its flow to a junction which leads to at least two outlet limbs of which at least one is a sample injection limb and another is a vent limb each of which outlet limbs comprises a restriction to fluid flow, passing carrier fluid at the same controlled pressure to each sample injection limb upstream of its restriction to fluid flow, the restrictions to fluid flow of the outlet limbs and the pressures downstream of them being such that the volumetric rate of flow through the vent limb is greater than that through the inlet limb the volumetric flow rate through which is greater than that through each sample injection limb, the volumetric flow rate of carrier fluid being at least equal to that through all of the sample injection limbs, and switching the supply of carrier fluid from a sample injection limb to the vent limb upstream of its restriction to fluid flow for a controlled time whilst maintaining the supply of carrier fluid to any other sample injection limb(s) thus injecting sample to the said sample injection limb, and switching the supply of carrier fluid from the vent limb to the sample injection limb to resume supply of carrier fluid through it, the temperature of the sample injection limb from the carrier fluid injection point to beyond the restriction to fluid flow being controlled.

The volume between the junction and the point at which carrier fluid is passed into the sample injection limb is preferably small. If it is negligible, the temperature sensitivity of the method (other than in the temperature controlled part of the sample injection limb) is also negligible. If it is not negligible, slight variation in sample sizes caused by variations of the temperature of the material in this volume may result, and it is preferred in this case to control the temperature in this volume also.

If the viscosity of the sample is very different from that of the carrier fluid, the volume between the point at which carrier fluid is introduced into the sample injection limb and the restriction to fluid flow of that limb should be at least sufficient to accommodate the required volume of sample.

The fluids are preferably gases or vapours.

The sample injection limbs may feed analytical devices of any kind or storage devices but very suitably feed chromatographic systems.

It will be understood that effluent from the vent limb may be recovered or further processed, for example, by returning it to the source of the material which is being sampled.

The restrictions to fluid flow may be packing of tubes, constrictions of the limbs, porous inserts, for example sintered glass plugs or discs, or may if desired be adjustable restrictions such as valves; it is preferred that valves should not be employed where there is any danger of corrosion but since it is not necessary to adjust any valve in the path of the sample during the process any corrosion which does occur and impairs the adjustability of the valve is unlikely to affect the analytical process which is being carried out.

The greater the difference in volumetric flow rate through the outlet limbs the greater the ability of the method to compensate for variations in the temperature and pressure of the source of the sample, and the lower the rate through the sample injection limb compared with that through the inlet limb the greater is the ability of the method to cope with reductions in the pressure and increases in the temperature of the source of sample. These factors should be chosen with reference to the likely variation in the temperature and pressure of the source of sample, but the only penalty associated with overdesign (the use of a very high flow rate of sample through the inlet limb compared with the volumetric flow rate through the sample injection limb and a low volumetric flow rate through the sample injection limb compared with a higher rate through the other limb) is loss of carrier and of sample.

It is preferred that the temperature of the sample injection limb be controlled upstream of the carrier fluid injection point more preferably at least as far as the junction since by this means sample passing to the sample injection limb is brought to its desired temperature more efficiently and the reproducability of the amounts injected is somewhat improved.

If desired the apparatus may be adapted to inject samples from a common source into different chromatographic systems by causing the sample injection limb to feed a flow switch as described in British Pat. No. 1,236,937; the flow switch may be operated to direct the sample at will into one of two or more chromatographic systems for analysis.

If it is desired to inject a sample, for example, to an analytical system at a pressure higher than that at the outlet of a sample injection limb, this may be achieved by passing the sample from the limb into a vessel to the inlet of which is subsequently fed a stream of carrier fluid at the desired pressure. The sample is thus carried onward at the higher pressure and surplus carrier fluid passes back to the junction.

One form of the invention will now be described with reference to the drawing which is a diagramtic representation of apparatus according to the invention.

A flow of material to be sampled is derived from source 1 which feeds the inlet limb 2 of junction 3. Inlet limb 2 comprises a resistance to fluid flow 4. From junction 3 a vent limb 5 which comprises a resistance to fluid flow 6 leads to the atmosphere and a sample injection limb 7 which comprises a resistance to fluid flow 8 leads to a chromatographic system 9 which is equipped with a detector for its effluent 10. Pressure controller 11 alternatively feeds sample injection limb 7 and vent limb 5 through lines 12 and 13 respectively. Limb 7 from the carrier fluid injection point is contained in a thermostat 14.

The resistances to fluid flow and the pressures downstream of the resistances are adjusted such that the volumetric rate of flow through the vent limb 5 is greater than that through the inlet limb 2 which in turn is greater than that through the sample injection limb 7.

At the beginning of the operation carrier fluid is fed through line 12 from constant pressure controller 11 to sample injection limb 7 upstream of resistance to fluid flow 8. Under these conditions the whole of the flow of sample passing through limb 2 passes to vent through vent limb 5. When it is desired to feed a sample from source 1 into chromatographic system 9 the carrier fluid flow from constant pressure controller 11 is switched from line 12 to line 13. Under these conditions the carrier fluid is passed to vent together with any surplus sample over and above that which passes down sample injection limb 7 and pure sample passes down sample injection limb 7. After a controlled time interval the flow of carrier fluid is switched from line 13 to 12 thus cutting off the supply of sample to sample injection limb 7 and resuming the flow of carrier fluid through that limb to chromatographic system 9. Surplus carrier fluid in this state of the system passes together with the whole of the material which is being sampled to vent through limb 5. The constant pressure controller 11 may if desired be replaced by a constant flow controller, if the pressure of the source of the material to be sampled is constant. The system is particularly advantageous for sampling gas sources since a constant molar quantity of gas is injected irrespective of variations in the temperature and pressure of the source if a constant pressure controller is used to supply a carrier gas.

The gas chromatographic system may comprise several columns and switching and/or back flushing facilities, if desired. The detector may be of any suitable type, for example it may be a flame ionisation detector.

The switching operation may be controlled by an operator or automatically. By using a constant time of injection a sample of constant size is injected. In the case of gaseous samples it is constant in terms of the number of gram molecules injected. In the case of liquid samples, a constant volume is injected in constant time.

Figure 2:
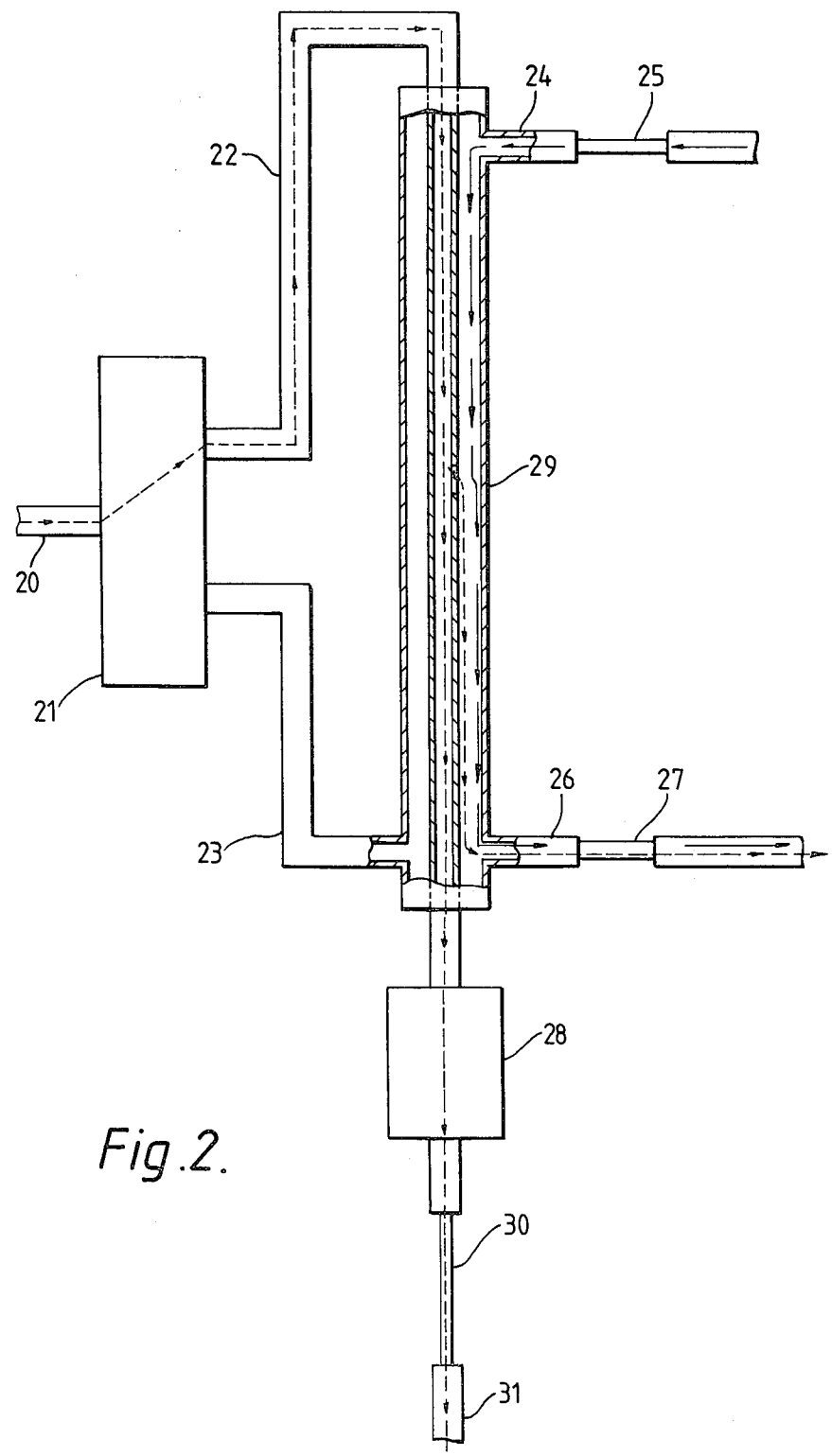

A suitable mechanical design for system which reduces the volume between the junction 3 and the point 15 to a negligible amount and provides a large volume between point 15 and restriction 8 will now be described with reference to FIG. 2, which shows schematically a cross section of the system in which the sample is switched to vent. Carrier supply pipe 20 feeds spool valve 21 which feeds pipes 22 and 23 alternatively. Pipe 22 leads through a sleeve 29 and volume 28 to sample injection limb 31 which comprises a restriction 30. At a mid point within sleeve 29 a hole passes through the wall of pipe 22. Pipe 23 feeds the outlet end of sleeve 29, which is provided with an inlet limb 24 which includes a restriction 25 at its inlet end. The outlet end of sleeve 29 feeds vent limb 26 which comprises a restrictor 27.

In normal operation, the stream to be sampled flows from inlet limb 24 through sleeve 29 to vent limb 26 whilst carrier fluid passes partly to the sample injection limb 30 and partly through the hole to sleeve 29 and vent limb 26. When sample is to be injected, the spool valve 20 is switched to feed carrier fluid to pipe 23, which causes part of the stream to be sampled to pass through the hole in the wall of line 22 to sample injection limb 31, whilst carrier fluid passes to vent together with the remainder of the stream which is being sampled. After a predetermined time interval the normal flow condition is restored thus completing the injection operation.

I claim:

1. A method of introducing a sample of controlled quantity so that reproducible sample quantities can be obtained regardless of variations in pressure and/or temperature, said method comprising the steps of:
   (a) passing a stream of sample fluid through a restriction to its flow to a junction which leads to at least two outlet limbs of which at least one of said outlet limbs is a sample injection limb and another is a vent limb, each of said outlet limbs comprising a restriction to fluid flow;
   (b) passing carrier fluid at a substantially constant pressure to each sample injection limb downstream of said junction and upstream of its restriction to fluid flow, the restrictions to fluid flow of the outlet limbs and the pressures downstream of them being such that the volumetric rate of flow of sample fluid and carrier fluid through the vent limb is greater than the volumetric rate of flow of sample fluid through the inlet limb, the volumetric flow rate of sample fluid through said inlet limb being greater than the flow rate through each sample injection limb, and the volumetric flow rate of carrier fluid being at least equal to the total of the volumetric flow rates through all of the sample injection limbs;
   (c) switching the supply of carrier fluid from a sample injection limb to the vent limb at a point downstream of said junction and upstream of its restriction to fluid flow for a controlled time while maintaining the supply of carrier fluid to any other sample injection limb thus injecting a portion of sample fluid to the first mentioned sample injection while the remainder of the sample fluid continues to flow through the vent limb;
   (d) switching the supply of carrier fluid switched according to step (c) from the vent limb to the sample injection limb to resume supply of carrier fluid, therethrough; and
   (e) controlling the temperature of the sample injection limb.

2. A method as in claim 1 in which a sample injection limb feeds a chromatographic system.

3. A method as in claim 1 in which the temperature of the sample injection limb is also controlled upstream of the carrier fluid injection point as far as the junction.

4. A process as in claim 1 in which steps (c) and (d) are practiced so that an effective volume of sample is utilized between the junction and the point at which carrier fluid is passed into the sample injection limb so that temperature variation of the sample volume will have negligible effect upon the reproducibility of the sample volume.

5. A method as in claims 1, 2, 3, or 4 which a sample is injected into an analytical system at a pressure higher than that at the outlet of the sample injection limb by passing the sample from the limb into a vessel to the inlet of which is subsequently fed a stream of carrier fluid at the desired pressure.

6. A method as in claim 1 in which the fluids are gases.

* * * * *